US012558344B2

(12) United States Patent
Yu et al.

(10) Patent No.: US 12,558,344 B2
(45) Date of Patent: Feb. 24, 2026

(54) COMPOSITION FOR PREVENTING OR TREATING BRAIN-NERVOUS SYSTEM DISEASES COMPRISING RITA OR DERIVATIVES THEREOF

(71) Applicant: DAEGU GYEONGBUK INSTITUTE OF SCIENCE AND TECHNOLOGY, Daegu (KR)

(72) Inventors: Seong Woon Yu, Daegu (KR); Seong Hee Jung, Busan (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 833 days.

(21) Appl. No.: 17/831,879

(22) Filed: Jun. 3, 2022

(65) Prior Publication Data

US 2022/0296569 A1 Sep. 22, 2022

Related U.S. Application Data

(63) Continuation of application No. PCT/KR2020/017476, filed on Dec. 2, 2020.

(30) Foreign Application Priority Data

Dec. 4, 2019 (KR) ........................ 10-2019-0160117

(51) Int. Cl.
*A61K 31/381* (2006.01)
*A61P 25/28* (2006.01)

(52) U.S. Cl.
CPC ............ *A61K 31/381* (2013.01); *A61P 25/28* (2018.01)

(58) Field of Classification Search
None
See application file for complete search history.

(56) References Cited

U.S. PATENT DOCUMENTS

2013/0331398 A1 12/2013 Morabito et al.
2018/0200251 A1 7/2018 Zhao et al.

FOREIGN PATENT DOCUMENTS

KR 10-2019-0143833 A 12/2019

OTHER PUBLICATIONS

Doggrell (Expert Opin. Investig. Drugs; 14(6):739-742, 2005).*
L Michel Espinoza-Fonseca"Targeting MDM2 by the small molecule RITA: towards the development of new multi-target drugs against cancer", Theoretical Biology and Medical Modelling 2005.
Sylvanie Surget et al.,"RITA (Reactivating p53 and Inducing Tumor Apoptosis) is efficient against TP53abnormal myeloma cells independently of the p53 pathway", Surget et al. BMC Cancer 2014.
Office Action by KIPO dated Dec. 26, 2021.
International Search Report PCT/ISA/210 for International Application No. PCT/KR2020/017476 dated Feb. 12, 2020.

* cited by examiner

*Primary Examiner* — Bong-Sook Baek
(74) *Attorney, Agent, or Firm* — Sughrue Mion, PLLC

(57) ABSTRACT

The present invention relates to a composition for preventing or treating central nerve system diseases, and by means of a compound according to one aspect, by inhibiting the death of adult hippocampal neural stem cells caused by stress and preserving the number of neural stem cells, the composition can be utilized in the prevention, amelioration, or treatment of mental diseases or neurodegenerative diseases, or in the prevention or amelioration of stress.

3 Claims, 4 Drawing Sheets

[FIG. 1]
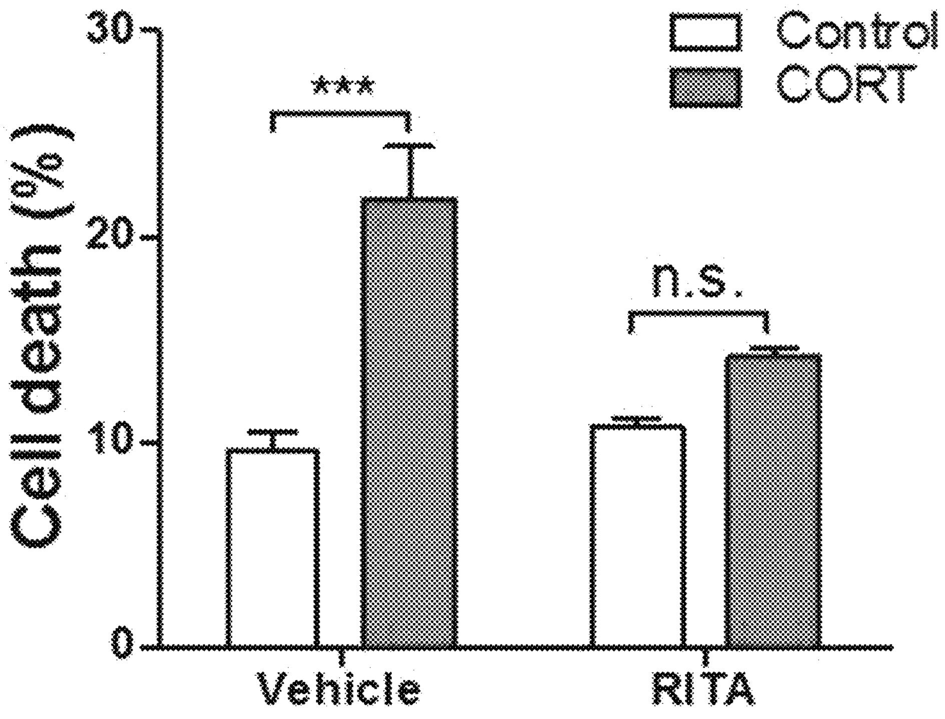

[FIG. 2]
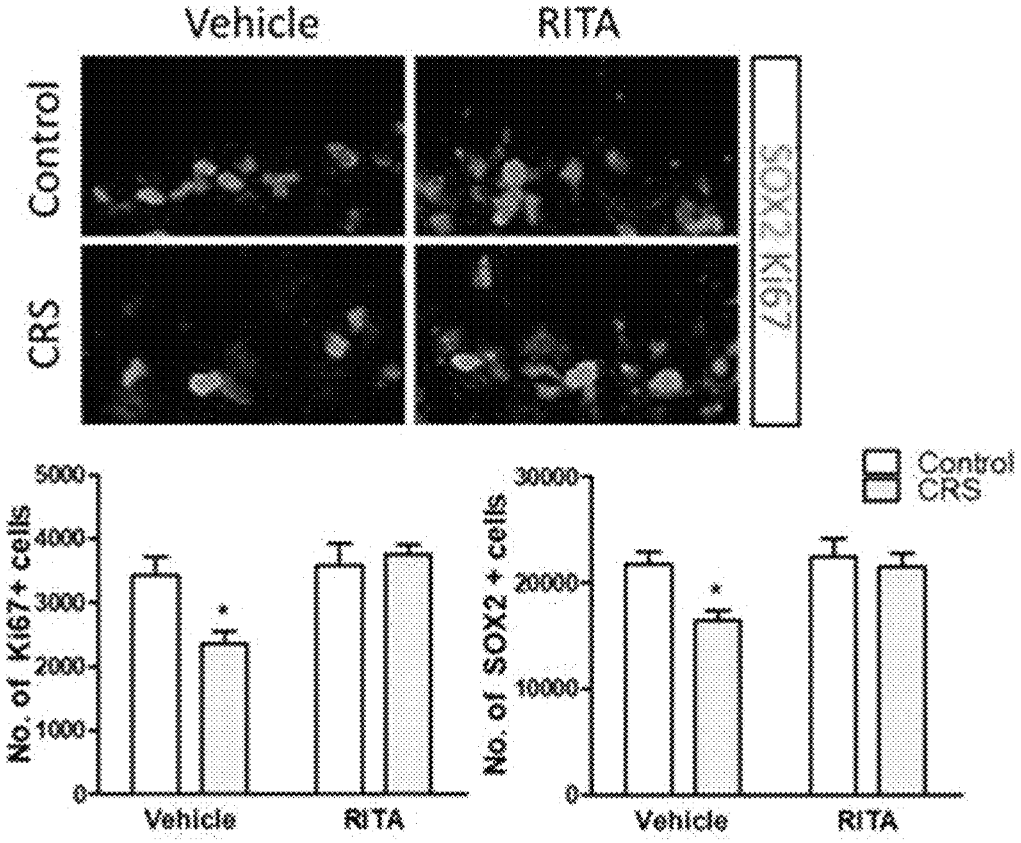

[FIG. 3]
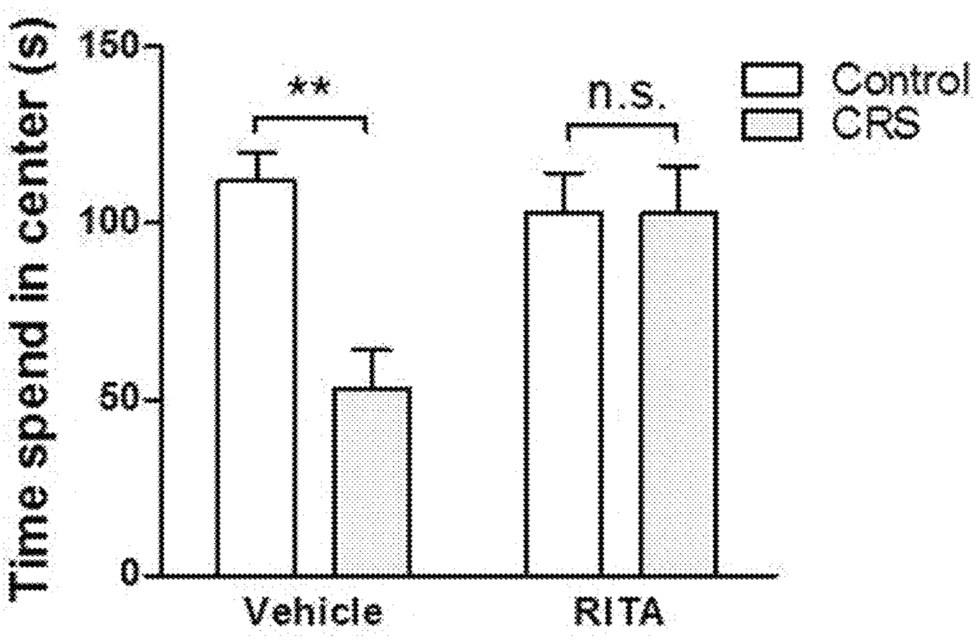

[FIG. 4]
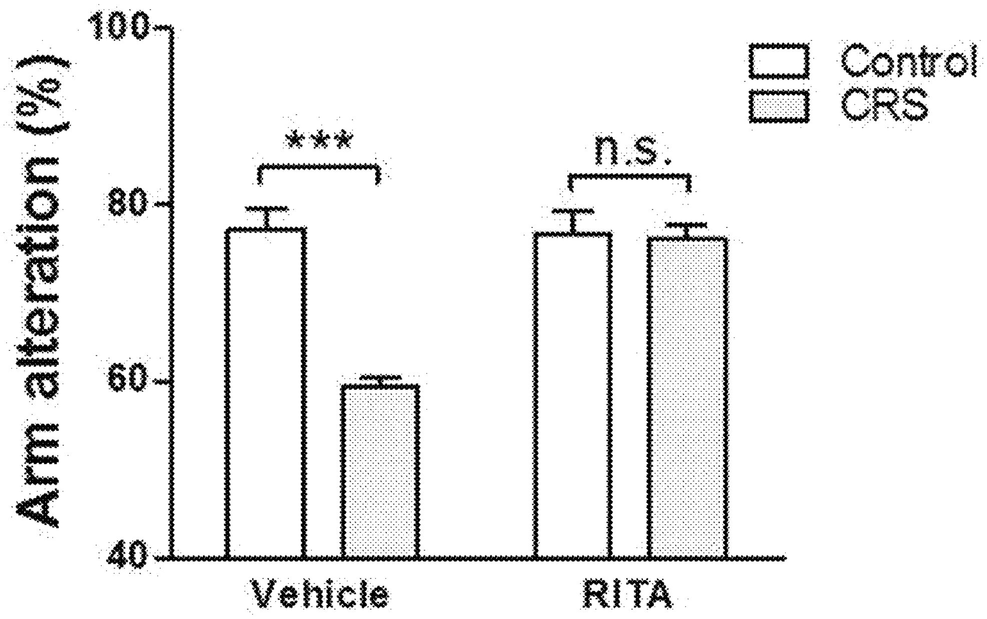

COMPOSITION FOR PREVENTING OR TREATING BRAIN-NERVOUS SYSTEM DISEASES COMPRISING RITA OR DERIVATIVES THEREOF

CROSS-REFERENCE TO RELATED APPLICATION

This application is a continuation of PCT International Application No. PCT/KR2020/017476 which has an International filing date of Dec. 2, 2020, and which claims priority to Korean patent application number 10-2019-0160117 filed Dec. 4, 2019, the entire contents of both of which are incorporated herein by reference.

TECHNICAL FIELD

The present invention relates to a composition for preventing or treating a brain-nervous system disease.

TECHNICAL FIELD

Adult hippocampal neural stem cells are susceptible to psychological stress. Stress-induced decrease in neural stem cells causes anxiety disorders and impaired learning ability, leading to various brain diseases.

A level of stress that the body can tolerate acts as an appropriate stimulant for our body, but strong and persistent physiological stress outside the acceptable range induces excessive secretion of glucocorticoids for a long time.

Since glucocorticoids secreted in excess for a long time degrade the body's immunity, resistance to external infection is reduced, and various diseases may be caused in our body. The glucocorticoids secreted in excess for a long time not only decrease immunity, but also cause brain cell damage and inhibit brain cell regeneration, leading to insomnia, lethargy, memory loss, depression, and even suicidal thoughts.

Brain-nervous system diseases such as a mental disorder or a degenerative brain disease are difficult to treat or prevent since their exact causes are unknown. However, stress is considered as one of the main causes of the brain-nervous system diseases.

Therefore, there is a demand for the development of new technology that can treat a brain-nervous system disease by inhibiting stress.

DISCLOSURE

Technical Problem

One aspect of the present invention provides a pharmaceutical composition for preventing or treating a brain-nervous system disease, which includes a compound represented by Formula 1, a solvate thereof, a stereoisomer, or a pharmaceutically acceptable salt thereof as an active ingredient.

Another aspect of the present invention provides a pharmaceutical composition for preventing or treating a stress-related disease, which includes a compound represented by Formula 1, a solvate thereof, a stereoisomer, or a pharmaceutically acceptable salt thereof as an active ingredient.

Still another aspect of the present invention provides a health functional food for preventing or improving a brain-nervous system disease, which includes a compound represented by Formula 1, a solvate thereof, a stereoisomer, or a sitologically acceptable salt thereof as an active ingredient.

Yet another aspect of the present invention provides a health functional food for preventing or relieving stress (e.g., mental stress), which includes a compound represented by Formula 1, a solvate thereof, a stereoisomer, or a sitologically acceptable salt thereof as an active ingredient.

Yet another aspect of the present invention provides a health functional food for improving memory, and preventing or improving an anxiety disorder, depression or cognitive dysfunction, which includes a compound represented by Formula 1, a solvate thereof, a stereoisomer, or a sitologically acceptable salt thereof as an active ingredient.

Yet another aspect of the present invention provides a quasi-drug composition for preventing or relieving stress (e.g., mental stress), which includes a compound represented by Formula 1, a solvate thereof, a stereoisomer, or a sitologically acceptable salt thereof as an active ingredient.

Yet another aspect of the present invention provides a method of preventing, improving or treating a brain-nervous system disease, which includes administering a composition including a compound represented by Formula 1, a solvate thereof, a stereoisomer, or a pharmaceutically acceptable salt thereof as an active ingredient into a subject.

Yet another aspect of the present invention provides a method of preventing, improving or treating a stress-related disease, which includes administering a composition including a compound represented by Formula 1, a solvate thereof, a stereoisomer, or a pharmaceutically acceptable salt thereof as an active ingredient into a subject.

Yet another aspect of the present invention provides a use of a compound represented by Formula 1, a solvate thereof, a stereoisomer, or a pharmaceutically acceptable salt thereof for preparing a composition for preventing, improving or treating a brain-nervous system disease.

Yet another aspect of the present invention provides a use of compound represented by Formula 1, a solvate thereof, a stereoisomer, or a pharmaceutically acceptable salt thereof for preparing a composition for preventing, improving or treating a stress-related disease.

Technical Solution

One aspect of the present invention provides a composition for preventing or treating a brain-nervous system disease, which includes a compound represented by Formula 1, a solvate thereof, stereoisomer or a salt thereof.

Another aspect of the present invention provides a composition for preventing, improving or treating a stress-related disease or preventing or relieving stress, which includes a compound represented by Formula 1, a solvate thereof, a stereoisomer or a salt thereof.

Formula 1 may have the following structural formula:

[Formula 1]

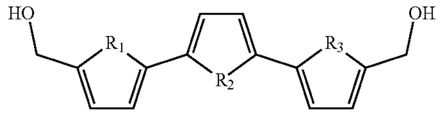

In this formula, $R_1$, $R_2$ and $R_3$ are each independently O or S.

In one embodiment, Formula 1 may be represented by Formula 2 below.

[Formula 2]

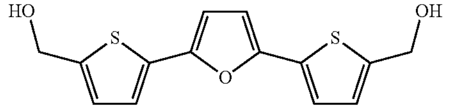

The IUPAC name of the compound of Formula 2 may be 2,5-bis[5-hydroxymethyl-2-thienyl] furan.

The term "stereoisomers" used herein refers to molecules that have the same chemical formula and the same binding sequences between constituent atoms, but have a different three-dimensional structure, and are classified as enantiomers and diasteromers. In addition, the stereochemically isomeric form of the pyridone derivative compound according to one embodiment defines all possible compounds that the compound of Formula 1 has. Unless stated or indicated otherwise, the chemical names of compounds refer to mixtures of all possible stereochemically isomeric forms, the mixtures include all diasteromers and enantiomers with a basic molecular structure. Particularly, the stereocenter may have the R- or S-configuration, and substituents on a divalent cyclic (partially) saturated radical may have the cis- or trans-configuration. A compound having a double bond may have E- or Z-stereochemistry at the double bond. The stereochemically isomeric form of the compound of Formula 1 is intended to be included within the scope of the present invention.

The term "prevention" used herein refers to all actions of inhibiting a brain-nervous system disease or a stress-related disease or delaying the onset thereof by administration of the pharmaceutical composition according to the present invention.

The term "treatment" used herein refers to all actions involved in alleviating or beneficially changing symptoms of a brain-nervous system disease or a stress-related disease by administration of the pharmaceutical composition according to the present invention.

The term "improvement" used herein refers to all types of actions that at least reduce parameters related to an abnormal condition, for example, the severity of a symptom. Here, the health functional food composition may be used simultaneously or separately with a drug for treatment before or after the onset of a brain-nervous system disease or a stress-related disease to prevent or improve the disease.

The brain-nervous system disease may include a mental disorder or a neurodegenerative disease.

The mental disorder may be a mental disorder caused by stress or a stress hormone (e.g., cortisol- or corticosteroid-based hormone). The stress may also be mental or physical stress.

The mental disorder may include all mental illnesses that increase the secretion of a stress hormone. Specifically, an example of the mental disorder may be selected from the group consisting of depression, hyperactivity, attention deficit, autism, post-traumatic stress disease (PTSD), anxiety disorders, sleep disorders, panic disorder, intellectual disability, memory loss, drug addiction, schizophrenia, obsessive compulsive disorder, megalomania, personality disorders, alcoholism, and manic depression.

The neurodegenerative disease may be selected from the group consisting of stroke, cognitive impairment, Alzheimer's disease, dementia with Lewy bodies, frontotemporal dementia, Parkinson's disease, Creutzfeldt-Jakob disease (CJD), Huntington's disease, multiple sclerosis, and Gillain-Barre Syndrome (GBS).

The stress-related disease may refer to a disease that may occur when changes occur in the functions of the autonomic nervous system and neuroendocrine system due to internal and external stimuli commonly used as stress, and the degree of such changes exceeds the acceptable value or persists for a long time. The stress-related disease may include mental disorders caused by stress, for example, lethargy, depression, panic disorder, sleep disorders, anxiety disorders, memory impairment, and malaise. In addition, the stress disease may include all of the physical symptoms caused by stress, such as fatigue, indigestion, and difficulty in breathing.

The compound of Formula 1 or Formula 2 according to one embodiment has an effect of inhibiting the death of neural stem cells in the hippocampus caused by a stress hormone, conserving the number of neural stem cells, or protecting neural stem cells. The decrease in neurogenesis by stress is due to the cell death of adult hippocampal neural stem cells caused by autophagy, and it has been reported that, when the autophagic cell death of adult hippocampal neural stem cells is inhibited, brain cognitive function and emotional disorders are prevented (Jung S et al., Autophagic death of neural stem cells mediates chronic stress-induced decline of adult hippocampal neurogenesis and cognitive deficits, Autophagy 16:512-530 (2020)). Therefore, by relieving the stress of a subject, the compound according to one embodiment may be effectively used in preventing, improving or treating a mental disorder or neurodegenerative disease, caused by the death of neural stem cells, or a stress-related disease, or preventing or relieving stress.

In one embodiment, the composition may be a pharmaceutical composition.

In the present specification, the "pharmaceutically acceptable" composition refers to a composition that is suitable to be used in contact with tissue of a subject (e.g., a human) due to a reasonable benefit/risk ratio without excessive toxicity, irritation, allergic responses or other problems or complications, and is included in the scope of sound medical judgment.

The term "pharmaceutically acceptable salt" used herein is an acid addition salt formed by a pharmaceutically acceptable free acid. The acid addition salt is obtained from inorganic acids such as hydrochloric acid, nitric acid, phosphoric acid, sulfuric acid, hydrobromic acid, hydroiodic acid, nitrous acid or phosphorous acid, aliphatic mono- and di-carboxylates, phenyl-substituted alkanoates, hydroxy alkanoates and alkane dioates, and non-toxic organic acids such as aromatic acids, aliphatic and aromatic sulfonic acids. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxylbenzoates, methoxybenzoates, phthalates, terephthalates, benzenesulfonates, toluenesulfonates, chlorobenzenesulfonates, xylenesulfonates, phenylacetates, phenylpropionates, phenylbutyrates, citrates, lactates, β-hydroxylbutyrates, glycholates, malates, tartrates, methanesulfonates, propanesulfonates, naphthalene-1-sulfonates, naphthalene-2-sulfonates or mandelates, but the present invention is not limited thereto.

The acid addition salt may be prepared by a conventional method, for example, by dissolving the compound represented by Formula 1 or 2 in an excessive amount of acidic aqueous solution, and precipitating the salt in a water-miscible organic solvent, for example, methanol, ethanol, acetone or acetonitrile. In addition, the acid addition salt may be prepared by evaporating a solvent or an excessive acid from the above mixture and then drying the resulting product or sucking and filtering a precipitated salt.

In addition, a pharmaceutically acceptable metal salt may be made using a base. An alkali metal or alkaline earth metal may be obtained by, for example, dissolving a compound in an excessive amount of an alkali metal hydroxide or alkaline earth metal hydroxide solution, filtering a non-dissolved compound salt, evaporating the filtrate, and drying it. Here, as the metal salt, a sodium, potassium or calcium salt is pharmaceutically suitable. The corresponding silver salt may be obtained by reacting an alkali metal or alkaline earth metal with a suitable silver salt (e.g., silver nitrate).

The pharmaceutical composition may include a pharmaceutically acceptable carrier in addition to the active ingredient. Here, the pharmaceutically acceptable carrier is one that is conventionally used in formulation, and includes lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxy benzoate, propyl hydroxy benzoate, talc, magnesium stearate, and mineral oil, but the present invention is not limited thereto. In addition, other than the above components, a lubricant, a wetting agent, a sweetening agent, a flavoring agent, an emulsifier, a suspending agent, or a preservative may be further included.

The pharmaceutical composition may be administered orally (oral preparation) or parenterally (e.g., intravenously, subcutaneously, intraperitoneally or locally in the form of an inhalant or injection) depending on a desired method, and for example, administered subcutaneously (that is, external preparations for skin) or orally (that is, oral preparation), but the present invention is not limited thereto.

As a buffer added to the various formulations, it is preferable to use a pH 5 to 9, isotonic, and non-irritating buffer. A dose of the pharmaceutical composition of the present invention may be selected according to a patient's condition and body weight, severity of a disease, a dosage form, an administration route and duration by those of ordinary skill in the art.

The pharmaceutical composition may be administered at a pharmaceutically effective amount. The term "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

The effective amount of the pharmaceutical composition according to the present invention may be changed according to a patient's age, sex, condition, and weight, the absorption of an active ingredient in the body, an inactivation rate, an excretion rate, a disease type, or a co-administered drug. The effective amount of the pharmaceutical composition according to the present invention may generally be in a range of 0.1 to 500 mg per kg of body weight a day, and may be administered daily or every other day and once to five times a day by dividing the daily dose. However, since the dose may be increased or decreased depending on an administration route, the severity of obesity, sex, a body weight or age, the above-mentioned dose does not limit the scope of the present invention in any way.

The food composition may introduce an active ingredient as is to food, or may be used together with another food or food ingredient, and may be appropriately used according to a conventional method. The mixing amount of the active ingredient may be appropriately determined depending on the purpose of its use (for prevention or improvement). Generally, in the production of food or beverages, the composition of the present invention is added in an amount of 60 wt % or less, and preferably 40 wt % or less with respect to a raw material. However, in the case of long-term intake for health and hygiene or health control, the amount may be below the above range.

In another embodiment, the composition may be a health functional food composition.

The food composition is not particularly limited in other components added other than containing the active ingredients as an essential component in the indicated ratio, and may contain additional components such as various flavoring agents or natural carbohydrates like a conventional beverage. Examples of the above-described natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, stevia extract (e.g., rebaudioside A, glycyrrhizin, etc.)] and synthetic sweeteners (saccharin, aspartame, etc.) may be advantageously used. The proportion of the natural carbohydrate may be appropriately determined by the choice of one of ordinary skill in the art.

Other than the above components, the food composition of the present invention may contain various nutrients, vitamins, minerals (electrolytes), flavoring agents including synthetic and natural flavoring agents, coloring agents, fillers (cheese, chocolate, etc.), pectic acid and a salt thereof, alginic acid and a salt thereof, organic acids, protective colloidal thickening agents, pH adjusters, stabilizers, preservatives, glycerin, alcohols, or carbonizing agents used in carbonated beverages, and such components may be used independently or in combination. The proportion of such an additive may also be suitably selected by those of ordinary skill in the art.

In another embodiment, the composition may be a quasi-drug.

The term "quasi-drug" refers to items corresponding to a textile, rubber product or the like used for the purpose of treating, alleviating, treating or preventing a human or animal disease; one that is not an instrument or machine or the like and acts weakly on the human body or does not act directly on the human body, and a preparation used for sterilization, insecticides or a similar purpose to prevent infection; and particularly, items, other than instruments, machines or devices, which are used for the purpose of diagnosing, curing, alleviating, treating or preventing a human or animal disease, or items other than instruments, machines or devices, which are used for the purpose of pharmacologically affecting a human or animal structure and function, and may also include external preparations for skin and personal hygiene products.

When the compound of Formula 1 is added to a quasi-drug composition for the purpose of preventing or improving a brain-nervous system disease or stress, the compound of Formula 1 may be added as is or used in combination with another quasi-drug component, and may be appropriately used according to a conventional method. The mixing amount of the active ingredient may be appropriately determined depending on the purpose of use (for protection, health or therapeutic treatment).

The quasi-drug composition includes, but not particularly limited to, a diffuser, a personal hygiene product, an external preparation for skin, a disinfectant cleanser, a shower foam, a mouth wash, a wet tissue, a detergent soap, a hand wash, a humidifier filter, a mask, an ointment or a filter filler. The external preparation for skin is preferably prepared in the form of an ointment, a lotion, a spray, a patch, a cream, a powder, a suspension, or a gel, but the present invention is not limited thereto. The personal hygiene product may be a soap, a wet tissue, a tissue paper, a shampoo, a toothpaste, a hair care product, an air freshener gel, or a cleaning gel.

Advantageous Effects

As a compound of one embodiment inhibits the death of adult hippocampal neural stem cells, caused by stress and conserves the number of neural stem cells, it can be effectively used in preventing, improving or treating a mental disorder or a neurodegenerative disease, or preventing or relieving stress.

DESCRIPTION OF DRAWINGS

FIG. 1 is a graph showing the degree of inhibiting the death of adult hippocampal neural stem cells caused by a stress hormone (corticosterone, CORT) after RITA treatment according to one embodiment.

FIG. 2 is a graph showing the effect of protecting neural stem cells by RITA injection according to one embodiment [Control, stress-experienced group (chronic restraint stress, CRS), vehicle (oil) only-injected stress-experienced group (vehicle CRS, and RITA-injected stress-experienced group (RITA CRS)].

FIG. 3 is a graph showing the anxiety-related behavior improvement result in an animal model by RITA injection, according to one embodiment (Control and CRS).

FIG. 4 is a graph showing the spatial memory improvement result in an animal model by RITA injection, according to one embodiment (Control and CRS).

MODES OF THE INVENTION

Hereinafter, the present invention will be described in further detail with reference to examples. However, these examples are merely provided to illustrate the present invention, and the scope of the present invention is not limited to the following examples.

Example 1. Analysis of Cell Death Inhibitory Activity of RITA in Stress Hormone-Induced Death of Hippocampal Neural Stem Cells Cell death inhibitory activity of RITA was confirmed in stress hormone-induced death of adult hippocampal neural stem.

All procedures in the management and use of laboratory animals were approved by the Animal Care and Use Committee of DGIST, and all animals were bred and used in a DGIST animal facility free of specific pathogens.

First, adult hippocampal neural stem cells (HCN cells; hereinafter, referred to as "HCN") were isolated from an 8-week-old female Sprague-Dawley rat (SD rat). Afterward, the isolated hippocampal neural stem cells were incubated using a serum-free medium containing Dulbecco's modified Eagle's medium (DMEM)/F-12 to which N2 and basic fibroblast growth factor (bFGF; PeproTech) were added in a 37° C. incubator. The cells were subcultured every 3 or 4 days.

The subcultured neural stem cells were put into a 96-well plate at $1.5\times10^5$ cells/ml, 50 nM RITA was treated together with 200 μM corticosterone (CORT), and cell death was confirmed after 48 hours. Before CORT treatment, 50 nM RITA was pre-treated for 3 hours and then treated again along with CORT.

For cell death assay, the cells were stained with Hoechst 33342 (Invitrogen) and propidium iodide (PI; Sigma) and photographed by a fluorescence microscope (Axiovert 40 CFL; Carl Zeiss), and the percentage of cell death was calculated by the following cell death (%) equation.

Cell death (%)=(the number of PI[red]-positive cells/the number of Hoechst [blue]-positive cells)×100

The result of cell death assay is shown in FIG. 1.

FIG. 1 is a graph showing the degree of inhibiting the death of adult hippocampal neural stem cells caused by a stress hormone (corticosterone, CORT) after RITA treatment according to one embodiment.

As shown in FIG. 1, it was able to be confirmed that the RITA compound according to one embodiment inhibits the death of neural stem cells caused by a stress hormone. As such, the effect of protecting hippocampal neural stem cells and inhibiting the stress hormone-mediated cell death shows that RITA according to one embodiment or a derivative compound thereof can be effectively used for stress hormone-induced mental disorders or brain-nervous system diseases including a neurodegenerative disease.

Example 2. Analysis of Protective Activity of RITA for Neural Stem Cells in Animal Model of Stress The protective activity of RITA for neural stem cells in a mouse experiencing stress was confirmed.

An 8-week-old male C57BL/6 mouse was subjected to chronic restraint stress (CRS) using a restrainer from 10 AM to 4 PM daily for 7 days. RITA (10 mg/kg) was intraperitoneally injected using a 1-ml syringe at 9:30 AM for 10 days from 3 days before the stress experience.

To confirm the number of hippocampal neural stem cells in the RITA-injected mouse, the control and the stress-experiencing mice were anesthetized by injecting the neuro-anesthetic Zoletil and the muscle anesthetic Rompun to isolate brain tissue. Afterward, the brain tissue was frozen with an optimal cutting temperature compound after fixing the brain with 4% paraformaldehyde (PFA). To perform immunohistochemistry, the frozen brain was cut in the coronal plane to a thickness of 40 μm, and then a neural stem cell indicator, SOX2, and a cell proliferation indicator, Ki67 protein, were labeled with Alexa488 or Alexa555 and stained. The number of fluorescence-expressing cells in the hippocampus of the stained brain was detected using a Confocal 780 microscope (Zeiss), and the result is shown in FIG. 2. As a control, oil, which is a medium in which RITA is dissolved, was injected.

FIG. 2 is a graph showing the effect of protecting neural stem cells by RITA injection according to one embodiment (Control, CRS).

As shown in FIG. 2, it was confirmed that the number of cells expressing SOX2, which is a stem cell indicator, and the number of cells expressing Ki67, which is a cell proliferation indictor, decreased by stress are considerably increased compared to the control. This means that the RITA compound according to one embodiment or a derivative thereof has a neural stem cell protective effect by inhibiting the death of neural stem cells caused by stress. Therefore, it can be seen that the RITA or a derivative thereof can be effectively used for a composition for relieving stress, and used in preventing or treating mental disorders or neurodegenerative diseases.

Example 3. Analysis of Activity of RITA for Improving Anxiety Disorder and Memory Impairment in Animal Model of Stress The effect of RITA for improving anxiety disorder and memory impairment in the animal model of Example 2 was analyzed.

Specifically, to measure anxiety-related behavior, an open field test was performed. The degree of anxiety was measured by observing a staying rate during a staying time in the middle in a square with a size of 40×40 $cm^2$ for 20 minutes. In addition, to measure spatial memory ability, a Y-Maze test was performed. The degree of spatial memory ability was measured by measuring the rate (arm alteration) entering each passage while freely moving in a Y-shaped maze space composed of three passages for 6 minutes. The results were measured using the EthoVision Observer and shown in FIGS. 3 and 4.

FIG. 3 is a graph showing the anxiety-related behavior improvement result in an animal model by RITA injection, according to one embodiment (Control and CRS).

FIG. 4 is a graph showing the spatial memory improvement result in an animal model by RITA injection, according to one embodiment (Control and CRS).

As shown in FIGS. 3 and 4, it was confirmed that the anxiety disorder-related behavior and spatial memory disability caused by stress experience were prevented by RITA treatment. Such a result shows that the RITA according to one embodiment or a derivative thereof can be effectively used in preventing or treating mental disorders and neurodegenerative diseases by improving anxiety disorders and cognitive impairment.

INDUSTRIAL AVAILABILITY

According to the present invention, RITA or a derivative thereof inhibits the stress-induced death of adult hippocampal neural stem cells and conserves the number of neural stem cells, and thus can be effectively used in a composition for preventing, improving or treating mental disorders or neurodegenerative diseases, or preventing or relieving stress.

The invention claimed is:

1. A method of treating an anxiety disorder or a memory impairment, comprising:

administering a composition comprising a compound represented by Formula 1 below, a solvate thereof, a stereoisomer or a pharmaceutically acceptable salt thereof as an active ingredient into a subject:

[Formula 1]

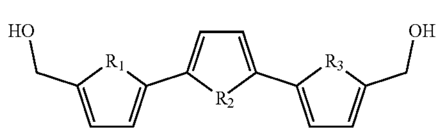

wherein $R_1$, $R_2$ and $R_3$ are each independently O or S and wherein the anxiety disorder or the memory impairment is caused by stress-induced death of adult hippocampal neural stem cells.

2. The method of claim 1, wherein the compound represented by Formula 1 is a compound represented by Formula 2 below:

[Formula 2]

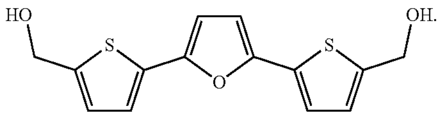

3. The method of claim 1, wherein the composition is a pharmaceutical composition or a quasi-drug composition.

* * * * *